(12) United States Patent
Louw

(10) Patent No.: US 11,364,176 B2
(45) Date of Patent: Jun. 21, 2022

(54) COMESTIBLE CAPSULE AND METHOD AND APPARATUS FOR MANUFACTURING SAME

(71) Applicant: COMBOCAP, INC., New York, NY (US)

(72) Inventor: Tobias Johan Louw, Morningside Heights, NY (US)

(73) Assignee: COMBOCAP, INC., New York City, NY (US)

(*) Notice: Subject to any disclaimer, the term of this patent is extended or adjusted under 35 U.S.C. 154(b) by 405 days.

(21) Appl. No.: 16/345,360

(22) PCT Filed: Oct. 16, 2017

(86) PCT No.: PCT/IB2017/056410
§ 371 (c)(1),
(2) Date: Apr. 26, 2019

(87) PCT Pub. No.: WO2018/078483
PCT Pub. Date: May 3, 2018

(65) Prior Publication Data
US 2019/0298613 A1 Oct. 3, 2019

(30) Foreign Application Priority Data
Oct. 27, 2016 (ZA) ................. 2016/07408

(51) Int. Cl.
A61J 3/07 (2006.01)
A61K 9/48 (2006.01)

(52) U.S. Cl.
CPC .............. A61J 3/074 (2013.01); A61J 3/072 (2013.01); A61K 9/4825 (2013.01)

(58) Field of Classification Search
None
See application file for complete search history.

(56) References Cited

U.S. PATENT DOCUMENTS

| 3,258,115 A | 6/1966 | Kath |
| 3,584,759 A * | 6/1971 | Lorincz ............... A61J 3/071 220/780 |
| 4,325,761 A | 4/1982 | Pace |
| 4,403,461 A | 9/1983 | Goutard et al. |
| 8,377,471 B2 | 2/2013 | Vanquickenborne et al. |
| 10,046,549 B2 * | 8/2018 | Van Rooyen ........ A61K 9/4808 |
| 2013/0186561 A1 | 7/2013 | Van Rooyen et al. |
| 2016/0287522 A1 | 10/2016 | Buydts et al. |

* cited by examiner

Primary Examiner — Aradhana Sasan
(74) Attorney, Agent, or Firm — Wood, Phillips, Katz, Clark & Mortimer

(57) ABSTRACT

A comestible gelatin capsule 10 for holding a substance in hermetic isolation includes a capsule body 12, a diaphragm 14 located within the capsule body and an end cap 16. Overlapping open end regions of walls 22 and 28 of the capsule body 12 and of the diaphragm 14, respectively, are fused to one another in a fusion welding process wherein the end regions undergo partial phase change so as to form a circumferential fused homogeneous sealing zone 36. The overlapping end regions are bent inwardly in the fusion welding process such that a portion of the wall 22 extends inwardly across a portion of the wall 28 thereby restricting axial movement of the capsule body and the diaphragm relative to one another forming a stable robust and effective hermetic seal.

15 Claims, 8 Drawing Sheets

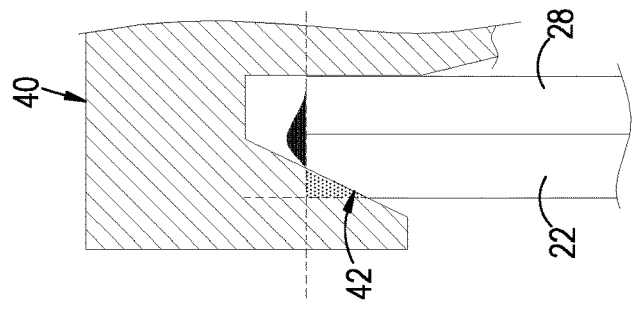
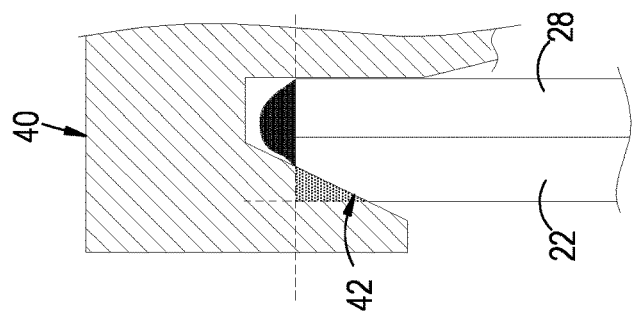
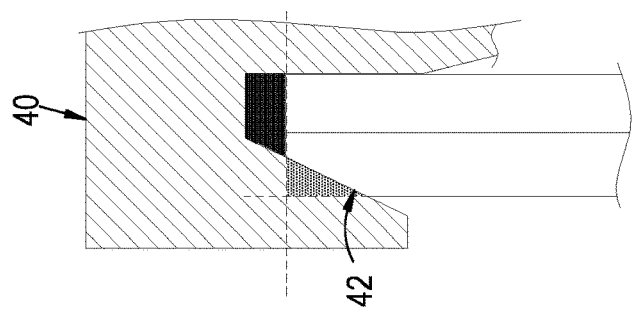
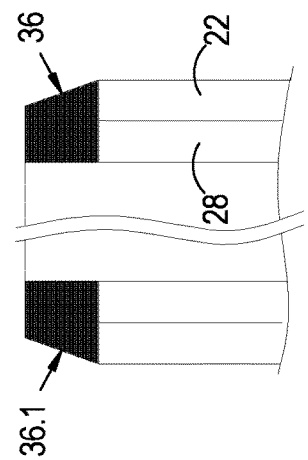

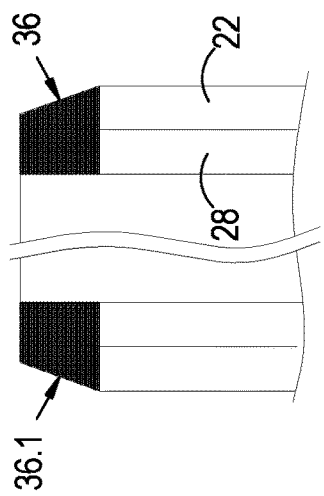
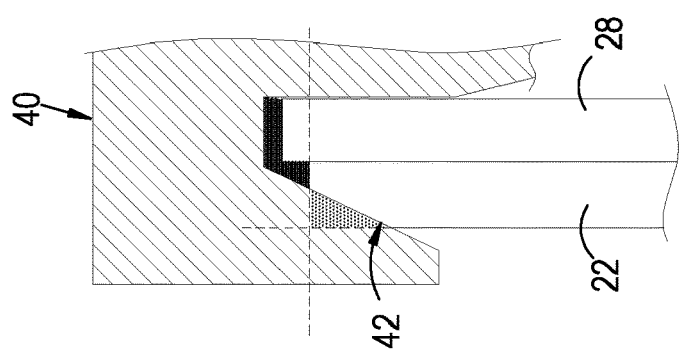
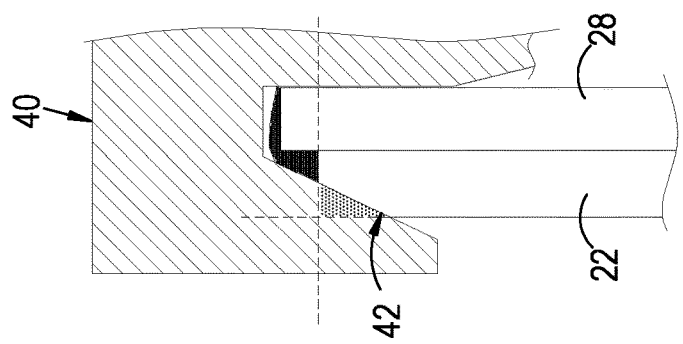
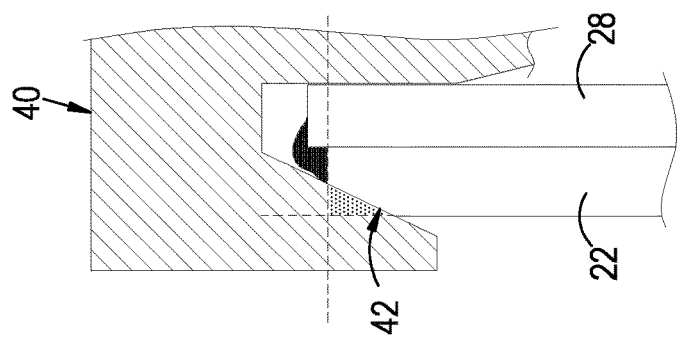

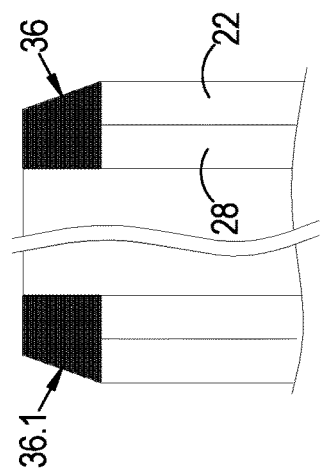
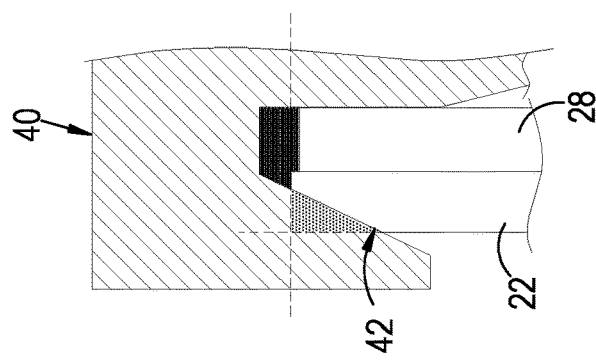
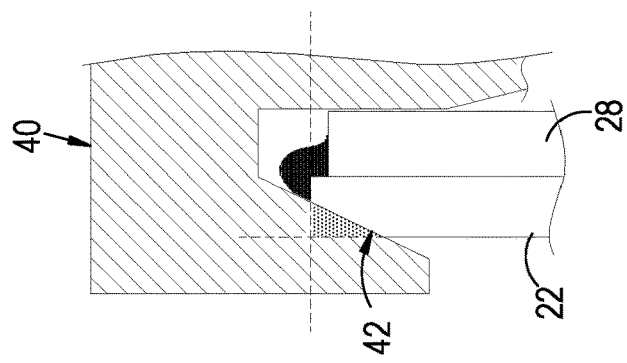
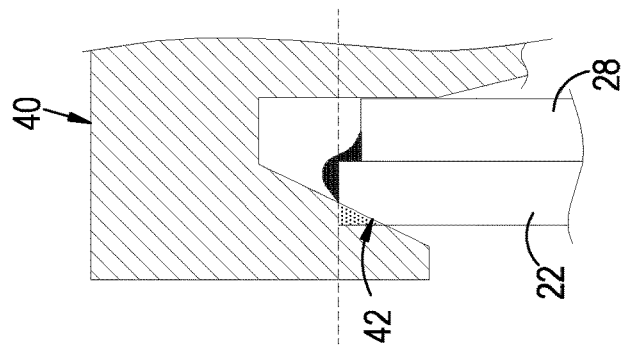

COMESTIBLE CAPSULE AND METHOD AND APPARATUS FOR MANUFACTURING SAME

FIELD OF INVENTION

This invention relates to a comestible capsule for holding a substance which is required to be held in hermetic isolation. It relates also to a method and apparatus for manufacturing a capsule for holding a substance which is required to be held in hermetic isolation.

SUMMARY OF INVENTION

According to a first aspect of the present invention there is provided a method of manufacturing a capsule for holding a substance that is required to be held in hermetic isolation, the method including the steps of:
providing a first capsule portion having a closed end and an opposed open end;
providing a second capsule portion having a closed end and an opposed open end;
at least partially filling the first capsule portion with the substance required to be held in hermetic isolation;
inserting the closed end of the second capsule portion into the open end of the first capsule portion such that a region of the second capsule portion is in overlapping contact with a region of the first capsule portion;
welding overlapping open end regions of the first and second capsule portions in a fusion welding process such that the end regions of the first and second capsule portions undergo partial phase change, so as to form a fused hermetic seal between the first and second capsule portions.

The fusion welding process may include plasticising the overlapping open end regions of the first and second capsule portions by applying heat to the overlapping open end regions and/or subjecting the overlapping end regions to one of microwave, radio-frequency or ultrasonic frequency wave energy so as to cause the end regions to undergo partial phase change.

The method may include bending the plasticised overlapping open end regions of the first and second capsule portions inwardly. More specifically, the method may include bending the overlapping open end regions of the first and second capsule portions inwardly along a circumference of the open end regions such that a portion of a wall of the first capsule portion extends inwardly across a portion of a wall of the second capsule portion, causing the wall of the first capsule portion to intersect the wall of the second capsule portion, thereby restricting axial movement of the capsule portions relative to one another.

The method may include a moulding step wherein the plasticised overlapping open end regions are moulded so as to form an annular fused sealing zone at the open end regions of the capsule portions.

The inward bending of the open end regions of the capsule portions may be achieved during the moulding step by moulding the overlapping open end regions in an inwardly bent configuration such that the fused sealing zone tapers inwardly from an outer side thereof.

The plasticising of the overlapping open end regions may be achieved by applying a heat sealing head to the overlapping open end regions of the first and second capsule portions thereby to plasticise the overlapping open end regions.

The heat sealing head may include a mould for moulding the plasticised overlapping end regions during the moulding step.

The first and second capsule portions may be of a fusion weldable material comprising a comestible gelatin based material.

According to a second aspect of the invention there is provided a method of sealing overlapping open end regions of two comestible capsule portions so as to form a sealed chamber wherein a substance is held in hermetic isolation, each of the capsule portions having an open end and a closed end wherein the closed end of one of the capsule portions is located within the other capsule portion such that the overlapping open end regions of the capsule portions are in contact, the method including welding the overlapping open end regions of the capsule portions in a fusion welding process such that the open end regions undergo partial phase change so as to form a fused hermetic seal between the first and second capsule portions.

The first and second capsule portions may be of gelatin.

The fusion welding process may include plasticising the overlapping open end regions of the first and second capsule portions by applying heat to the overlapping open end regions and/or subjecting the overlapping end regions to one of microwave, radio-frequency or ultrasonic frequency wave energy so as to cause the end regions to undergo partial phase change.

The method may include bending the plasticised overlapping open end regions of the first and second capsule portions inwardly. More specifically, the method may include bending the overlapping open end regions of the first and second capsule portions inwardly along a circumference of the open end regions such that a portion of a wall of the first capsule portion extends inwardly across a portion of a wall of the second capsule portion, causing the wall of the first capsule portion to intersect the wall of the second capsule portion, thereby restricting axial movement of the capsule portions relative to one another.

The method may include a moulding step wherein the plasticised overlapping open end regions so as to form an annular fused sealing zone at the open end regions of the capsule portions.

The inward bending of the open end regions of the capsule portions may be achieved during the moulding step wherein the overlapping regions are moulded in an inwardly bent configuration such that the fused sealing zone tapers inwardly from an outer side thereof.

The plasticising of the overlapping open end regions may be achieved by applying a heat sealing head to the overlapping open end regions of the first and second capsule portions thereby to plasticise the overlapping open end regions.

The heat sealing head may include a mould for moulding the plasticised overlapping end regions during the moulding step.

According to a third aspect of the invention there is provided a comestible capsule including:
a first comestible capsule portion having a closed end and an open end; and
a second comestible capsule portion having a closed end and an open end, the second capsule portion being located within the first capsule portion such that a region of the second capsule portion is in overlapping contact with a region of the first capsule portion so as to define a chamber within which a substance is held in hermetic isolation, the capsule being characterized in that overlapping open end regions of the first and second capsule portions are fused to one another so as to form a circumferential fused sealing zone.

The first and second capsule portions may be of gelatin.

The fused sealing zone may taper inwardly from an outer side thereof towards a free end of the fused sealing zone.

The overlapping end regions of the first and second capsule portions may be fused to one another by being plasticised such that the fused sealing zone comprises a homogeneous sealing zone.

The capsule may include an end cap which is located over the open ends of the first and second capsule portions thereby to define an additional chamber within which an additional substance can be held.

The capsule may be manufactured in accordance with the method in accordance with the first aspect of the invention.

The capsule may be sealed in accordance with the method of sealing in accordance with the second aspect of the invention.

According to a fourth aspect of the invention there is provided a sealing apparatus for sealing overlapping open end regions of two capsule portions so as to form a sealed chamber wherein a substance is held in hermetic isolation, each of the capsule portions having an open end and a closed end wherein the closed end of one of the capsule portions is located within the other capsule portion such that the overlapping open end regions are in contact, the sealing apparatus comprising a heat sealing head including a mould defining a mould cavity within which the overlapping open end regions of the capsule portions are received, the heat sealing head being operable to apply heat to the overlapping open end regions in a fusion welding process sufficient to cause plasticising of the overlapping open end regions, causing the end regions to undergo partial phase change thereby to fuse the overlapping open end regions to form a circumferential annular sealing zone.

The two capsule portions may be of gelatin.

The mould cavity of the heat sealing head may be in the form of a circumferential groove.

The mould may define an inner moulding wall an outer moulding wall and an end moulding wall extending between the inner and outer moulding walls, the inner moulding wall contacting an inner side of the overlapping open end regions of the capsule portions, the outer moulding wall contacting an outer side of the overlapping open end regions of the capsule portions for applying heat to and forming the inner and outer sides of the overlapping open end regions of the capsule portions to form said fused sealing zone.

The outer moulding wall may define a moulding face which extends obliquely relative to the outer side of the overlapping open end regions, thereby to bend the overlapping end regions inwardly providing the fused sealing zone with a tapering configuration wherein
the fused sealing zone tapers inwardly from an outer side thereof towards a free end of the fused sealing zone.

The sealing apparatus may be configured to seal overlapping end regions of the first and second capsule portion of the capsule in accordance with the third aspect of the invention.

BRIEF DESCRIPTION OF THE DRAWINGS

Further features of the invention are described hereinafter by way of a non-limiting example of the invention, with reference to and as illustrated in the accompanying diagrammatic drawings. In the drawings:

FIGS. 6A-6C show sectional side views of the heat sealing head of FIG. 3 and overlapping end regions of capsule portions wherein the ends of the inner and outer capsule portions are aligned flush with one another, illustrating, in sequence, the manner in which the overlapping open end regions of the capsule of FIG. 3 are fused so as to form a fused sealing zone at the open end regions of the capsule portions;

FIG. 6D shows a fragmentary sectional side view of the fused open end regions of the capsule portions shown in FIG. 6C;

FIG. 7A-7C show sectional side views of the heat sealing head of FIG. 3 and overlapping open end regions of capsule portions wherein the end of the diaphragm projects beyond an end of the capsule body, illustrating, in sequence, the manner in which a fused sealing zone is formed at the open end regions of the capsule portions;

FIG. 7D shows a fragmentary sectional side view of the fused open end regions of the capsule portions shown in FIG. 7C;

FIGS. 8A-8C show sectional side views of heat sealing head of FIG. 3 and overlapping open end regions of capsule portions wherein the end of the capsule body projects beyond the end of the diaphragm, illustrating, in sequence, the manner in which a fused sealing zone is formed at the open end regions of the capsule portions;

FIG. 8D shows a fragmentary sectional side view of the fused open end regions of the capsule portions shown in FIG. 8C;

DETAILED DESCRIPTION OF THE INVENTION

Figure 1:
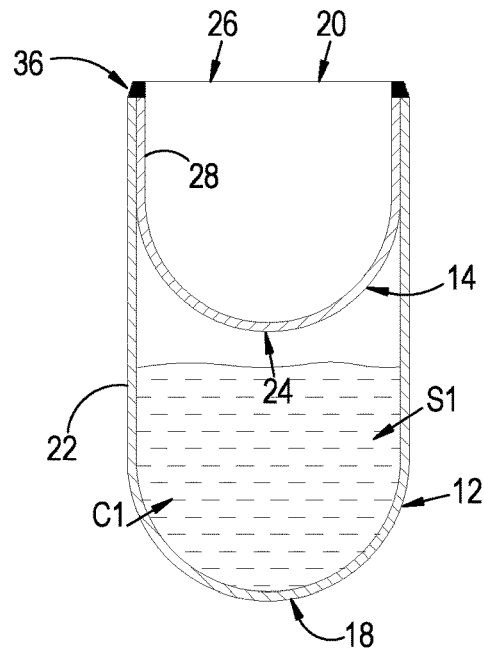
FIG. 1 shows a schematic representation of a sectional side view of two capsule portions of a comestible gelatin capsule in accordance with the invention, which define a chamber for holding a substance in hermetic isolation.
Figure 2:
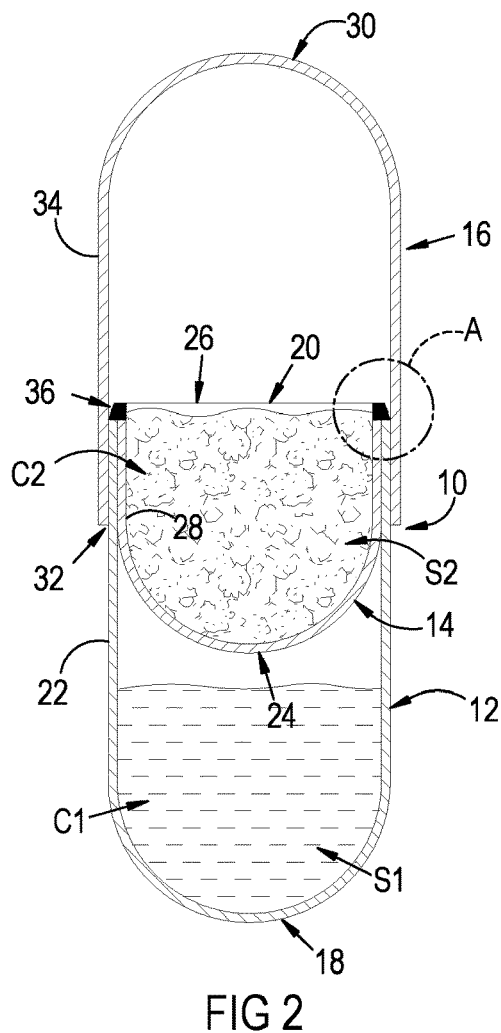
FIG. 2 shows the gelatin capsule portions of FIG. 1, including an end cap which closes off open ends of the capsule portions thereby to define a second chamber for holding a second substance in hermetic isolation.
Figure 2A:
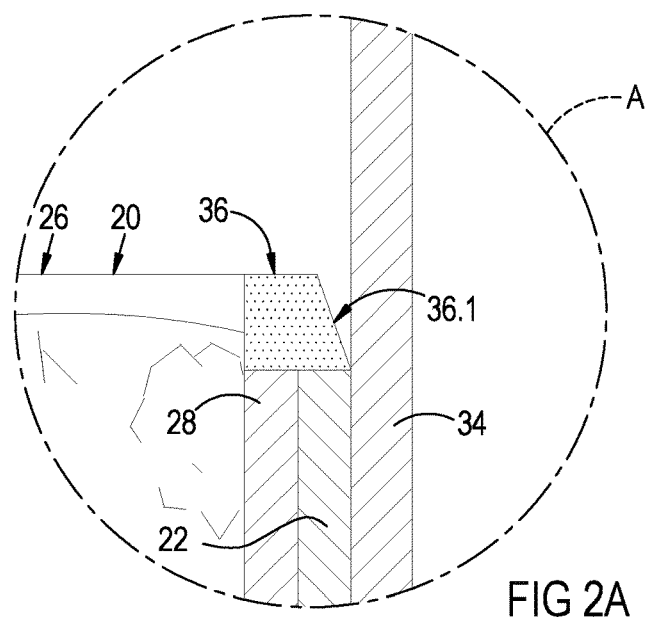
FIG. 2A shows an enlarged sectional side view of detail A of FIG. 2.
Figure 3:
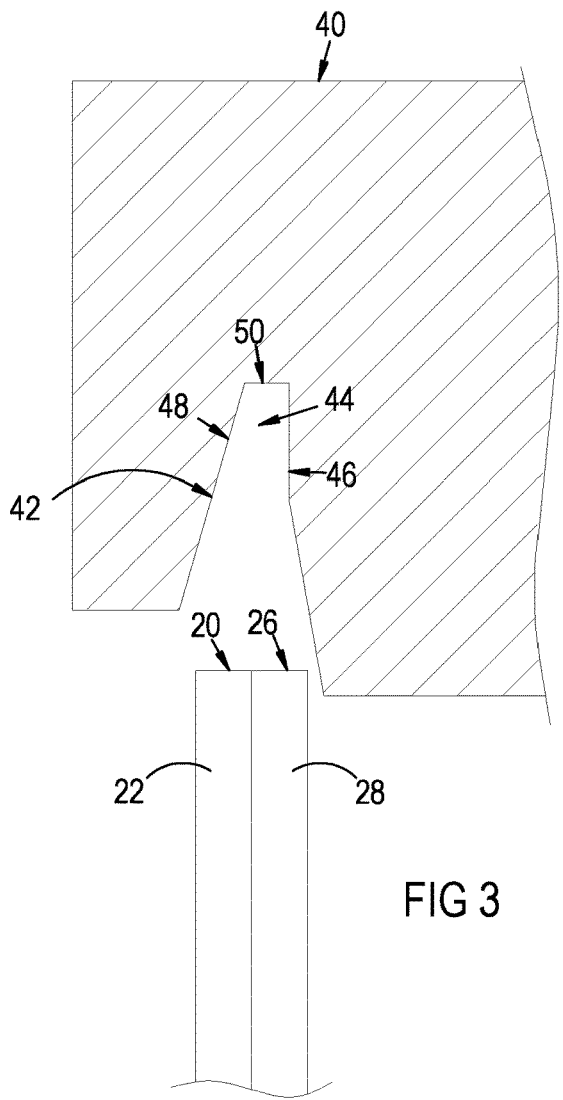
FIG. 3 shows a sectional side view of a heat sealing head of a sealing apparatus in accordance with the invention and a fragmentary sectional side view of open end regions of a capsule wherein the open ends are flush aligned prior to entering a mould cavity of the heat sealing head.

With reference to the drawings, a comestible capsule in accordance with the invention, is designated generally by the reference numeral 10. The capsule 10 includes a first capsule portion in the form of a capsule body 12 of flexible comestible gelatin, a second capsule portion in the form of a diaphragm 14 of flexible comestible gelatin which is located within the capsule body 12 and an end cap 16. The gelatin of the first and second capsule portions is fusion weldable. In a particular example, the first and second capsule portions may be of a hard gelatin material obtained by hydrolysis of collagen obtained from animal connective tissue, bone and/or pork skin and may include a plasticizer such as glycerol.

The capsule body 12 has a domed closed end 18 and an open end 20 and a cylindrical side wall 22 which extends between the ends 18, 20. The diaphragm 14 has a domed closed end 24 and an open end 26 and includes a cylindrical side wall 28 that extends between the closed and open ends 24, 26. The end cap 16 has a domed closed end 30 and an open end 32 and a cylindrical side wall 34 which extends between the closed and open ends 30, 32. A compartment C1 is defined by the capsule body 12 and the diaphragm 14 for holding a substance S1 therein while a compartment C2 is defined by the diaphragm 14 and the end cap 16 for holding a second substance S2 therein.

Open end regions of the side walls 22 and 28 of the capsule body 12 and the diaphragm 14, respectively, overlap and abut one another. Furthermore, end regions of the side walls 34 and 22 of the end cap and the capsule body 12, respectively, overlap and abut one another. Overlapping regions of the side walls 22 and 28 and of the side walls 34 and 22 are thus in contact with one another.

The substance S1 is required to be held in hermetic isolation within the chamber C1. While contact between of the overlapping open end regions of the walls 22 and 28 of the capsule body 12 and the diaphragm 14, respectively, provides for a degree of sealing between the walls, this is insufficient to provide for a stable hermetic seal between the diaphragm and the capsule body. As such, overlapping open end regions of the walls 22 and 28 of the capsule body 12 and the diaphragm 14, respectively, are fused to one another in a fusion welding process so as to form a circumferential fused homogeneous sealing zone 36. The fused sealing zone 36 tapers inwardly from an outer side thereof towards a free end of the sealing band so as to define a circumferential tapered outer face 36.1. The side wall 34 of the end cap 16 is thus pushed over the fused sealing zone at the open ends of the capsule body 12 and the diaphragm 14 so as to overlap an outer side of the side wall 22 of the capsule body.

Figure 4:
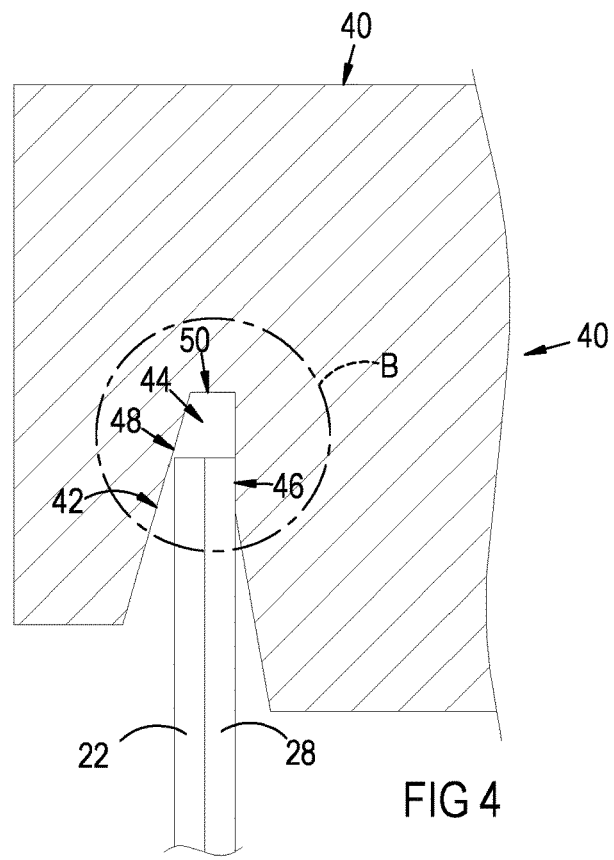
FIG. 4 shows a sectional side view of the heat sealing head and capsule of FIG. 3 after the capsule has been received further into the mould cavity of the heat sealing head.
Figure 5:
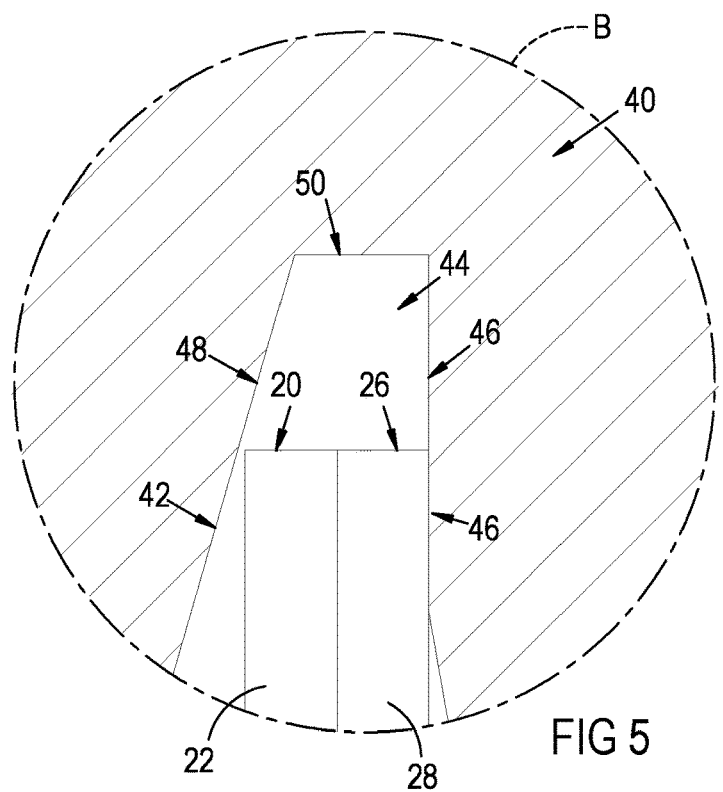
FIG. 5 shows an enlarged sectional side view of detail B of FIG. 4.

With reference to FIGS. 4 to 6 of the drawings, a method of manufacturing the gelatin capsule 10 in accordance with the invention, is shown. The method includes providing the capsule body 12 and the diaphragm 14. The capsule body is partially filled with the substance S1 which is required to be held in hermetic isolation. The closed end 24 of the diaphragm is then inserted into the open end 20 of the capsule body such that the side wall 28 of the diaphragm is in overlapping contact with the side wall 22 of the capsule body until the open ends 20 and 26 are aligned flush with one another.

The overlapping open end regions of the capsule body 12 and the diaphragm 14 are plasticised in a fusion welding process such that the open end regions undergo a partial phase change. The plasticised overlapping end regions are then fused so as to form the fused sealing zone 36. In the method of manufacturing the gelatin capsule, a sealing apparatus comprising a heat sealing head 40 is used to fuse and form overlapping open end regions of the capsule body 22 and the diaphragm 28. The heat sealing head includes a mould 42 defining a mould cavity 44 within which the overlapping end regions of the capsule body 22 and the diaphragm 28 are received and moulded. More specifically, the mould cavity of the heat sealing head is in the form of an annular groove. The mould 42 defines an inner moulding wall 46, an outer moulding wall 48 and an end moulding wall 50 extending between the inner and outer moulding walls. The inner moulding wall 46 contacts and moulds an inner side of the overlapping open end regions of the diaphragm 28, while the outer moulding wall 48 contacts an outer side of the overlapping open end regions of the capsule body. The end moulding wall 50 extends perpendicularly relative to the inner moulding wall 46 when viewed in cross-section while the outer moulding wall 42 defines a moulding face which extends obliquely relative to the end moulding wall 50 so as to define an obtuse angle between the outer moulding wall and the end wall when viewed in cross-section.

With reference to FIG. 6A-6C of the drawings, the manner in which the overlapping end regions of the capsule body and the diaphragm, respectively, are fused in a fusion welding process and moulded so as to form the fused circumferential sealing band 36 at the open end regions of the walls 22, 28 is illustrated. The overlapping end regions of the walls 22, 28 are received within the mould cavity. The heat sealing head heats the overlapping open end regions to a temperature wherein the end regions are plasticised and melded such that the end regions undergo partial phase change. The plasticised end regions are shown in darker shades in the drawings. As the overlapping end regions of the capsule body and the diaphragm are received further within the mould cavity, further plasticizing of the end regions takes place until the plasticised material of the end regions completely fills the mould cavity, with the mould forming the sealing band 36 in the process. The plasticised material is thereafter allowed to cool forming a homogeneous fused annular sealing band which defines a rim of the fused ends of the diaphragm and the capsule body. The resultant fused sealing zone 36 is shown in FIG. 6D.

The capsules 10 are manufactured in a batch process wherein a batch of capsule bodies 12 are stably supported in a tray, with the diaphragms 14 being inserted into the open ends of the capsule bodies. The head sealing head 40 is lowered onto the overlapping open end regions of the diaphragm and the capsule body. As the sealing head is lowered onto the end regions of the diaphragm and the capsule body, an outer side of the wall 22 of the capsule body initially contacts the outer moulding wall 48 causing heat to be transformed from the heat sealing head to the capsule body initiating the plasticising process. As the heat sealing head is lowered into the overlapping end regions of the diaphragm and the capsule body, a nominal clearance 28 is maintained between an outer side of the wall 28 of the diaphragm 14 and the inner moulding wall 46 so as to maintain structural integrity of the wall 28 as the heat sealing head is lowered. In another embodiment of the invention, the heat sealing head may have different heat zones, with a lower temperature zone being located adjacent the inner moulding wall so as to lower the temperature of the wall 28 relative to the wall 22.

Figure 9:
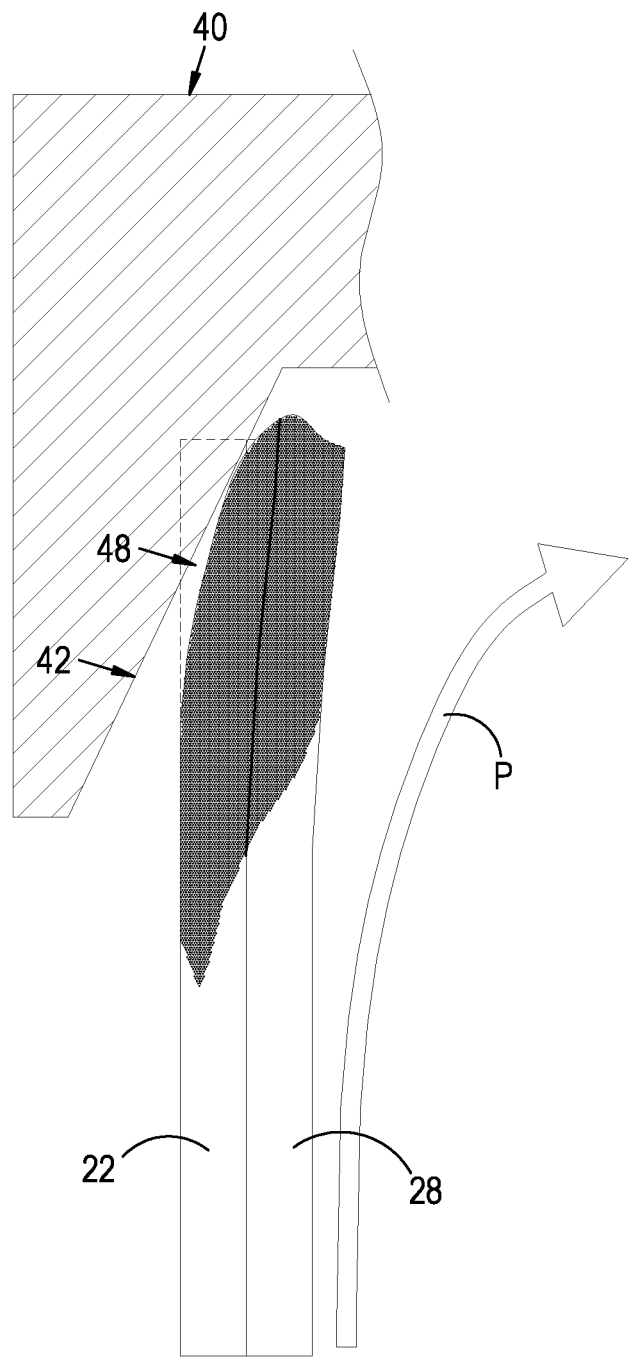
FIG. 9 shows an enlarged fragmentary sectional side view of overlapping open end regions of the capsule portions shown in FIG. 6, illustrating the manner in which the walls of the capsule portions bow inwardly.
Figure 10:
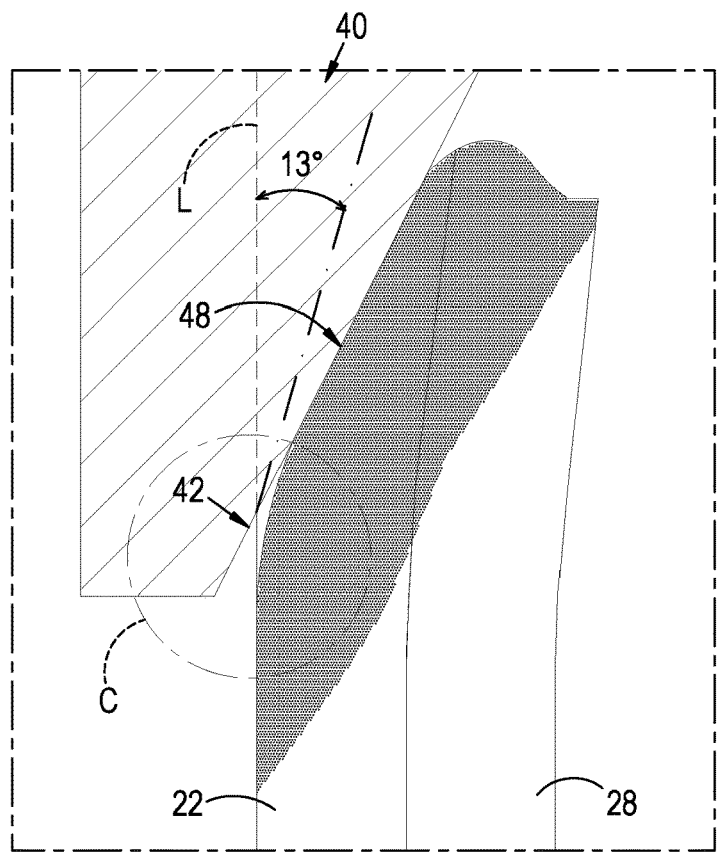
FIG. 10 shows an enlarged fragmentary sectional side view of an upper end region of the overlapping open end region of the capsule portions, illustrating the direction of lateral forces acting on the open end regions.
Figure 10A:
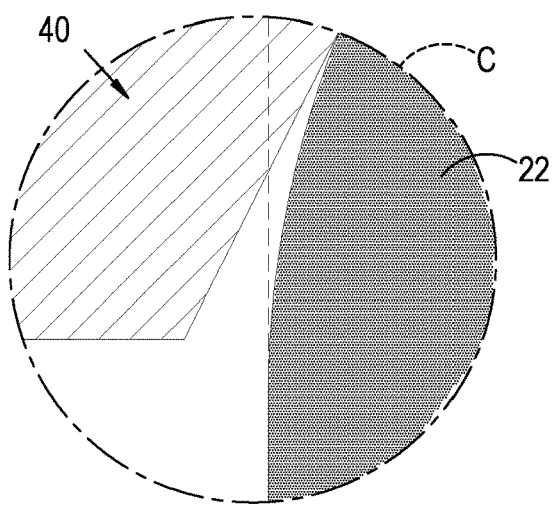
FIG. 10A shows detail C of FIG. 10.

Lowering of the heat sealing head onto the overlapping open end regions of the diaphragm and the capsule body, causes the angled outer moulding wall 48 of the heat sealing head to apply a lateral force to the wall 22 of the capsule body causing inward bending of the walls 22 (indicated by arrow P) as shown in FIGS. 9, 10 and 10A, towards the wall 28 of the diaphragm. The lateral forces together with softening of the capsule body and the diaphragm due to heat transfer from the heat sealing head, causes inward bending of the walls 22 and 28 resulting in the widths of the walls 22 and 28 being relatively narrower at end regions thereof. As such, a portion of the softened wall 22 of the capsule body extends across the wall 28 of the diaphragm thereby restricting relative axial movement between the diaphragm and the capsule body and providing a strong bond between the walls 28 and 22 of the diaphragm and the capsule body, respectively. Contact with the angled outer moulding wall 48 causes deviation of the walls 22 and 28 through an angle of about 13° as shown in FIG. 10.

Fusion of the open end regions of the walls 22 and 28 is achieved due to plasticisation of the end regions due to heat transfer from the heat sealing head. This is achieved due to partial phase change of the gelatin from solid crystalline to liquid making the material pliable and malleable. As the heat sealing head is lowered, heat is transferred to the wall 22 and radiates inwardly therefrom to the wall 28. Heat transfer from the heat seal head continues to radiate through the walls causing the two walls 22 and 28 to blend in a uniform plasticised state typical of a partial phase change of gelatin.

With reference to FIG. 7A-7C, the manner in which overlapping end regions 22, 28 of the capsule body and the diaphragm, respectively, are fused and moulded wherein the end 26 of the wall 28 projects beyond the end 20 of the wall 22. The fusion process is the same as that shown in FIGS. 6A-6C, with the resultant fused sealing bond 36 being shown in FIG. 7D.

With reference to FIG. 8A-8C, the manner in which overlapping end regions 22, 28 of the capsule body and the diaphragm, respectively, are fused and moulded wherein the end 20 of the wall 22 projects beyond the end 26 of the wall 28. The fusion process is the same as that shown in FIGS. 6A-6C, with the resultant fused sealing bond 36 being shown in FIG. 8D.

The fused sealing bond forms a stable, robust and effective hermetic seal for the chamber C1 thereby ensuring that the substance S1 is held in hermetic isolation. The circumferentially-extending tapered outer face 36.1 provides a chamfer permitting easier displacement of the capsule body when capping the capsule body with the end cap 16.

The fusion of the overlapping open end regions of the diaphragm and the capsule body provides a strong bond between the overlapping end regions preventing relative movement between the diaphragm and the capsule body thereby ensuring that the volume of the chamber C1 remains constant particularly in circumstances wherein ambient temperature or pressure conditions may be variable or where external physical forces are extended on the capsule.

Inward bending of upper end regions of the overlapping end regions of the capsule portions restricts axial displacement of the diaphragm relative to the capsule body.

The fusion process described hereinabove provides for even homogenous fusion of the overlapping end regions of the diaphragm and the capsule body resulting in a dimensionally accurate and uniform fused sealing zone which defines a rim of the fused capsule body and diaphragm.

This dimensional accuracy and uniformity is critical to ensure that capping clearance tolerances are adhered to which comply with industry standard requirements for dry filling and recapping machinery. A clearance gap of 0.03 mm is typically required for recapping a capsule body with a circumferential dimensional tolerance of 0.01.

The invention claimed is:

1. A method of manufacturing a comestible capsule for holding a substance that is required to be held in hermetic isolation, the method including the steps of:
   providing a first comestible capsule portion having a closed end and an opposed open end;
   providing a second comestible capsule portion having a closed end and an opposed open end;
   at least partially filling the first capsule portion with the substance required to be held in hermetic isolation;
   inserting the closed end of the second capsule portion into the open end of the first capsule portion such that a region of the second capsule portion is in overlapping contact with a region of the first capsule portion;
   welding overlapping open end regions of the first and second capsule in a fusion welding process such that the end regions of the first and second capsule portions undergo partial phase change so as to form a fused hermetic seal between the first and second capsule portions, the method being characterised in that it includes bending the plasticised overlapping open end regions of the first and second capsule portions inwardly along a circumference of the open end regions such that a portion of a wall of the first capsule portion extends inwardly across a portion of a wall of the second capsule portion, causing the wall of the first capsule portion to intersect the wall of the second capsule portion, thereby restricting axial movement of the capsule portions relative to one another.

2. The method according to claim 1, wherein the fusion welding process includes plasticising the overlapping open end regions of the first and second capsule portions by applying heat to the overlapping open end regions and/or subjecting the overlapping end regions to one of microwave, radio-frequency or ultrasonic frequency wave energy so as to cause the end regions to undergo partial phase change.

3. The method according to claim 1, which includes a moulding step wherein the plasticised overlapping open end regions are moulded so as to form an annular fused sealing zone at the open end regions of the capsule portions.

4. The method according to claim 3, wherein the inward bending of the open end regions of the capsule portions is achieved during the moulding step by moulding the overlapping open end regions in an inwardly bent configuration such that the fused sealing zone tapers inwardly from an outer side thereof.

5. The method according to claim 4, wherein the plasticising of the overlapping open end regions is achieved by applying a heat sealing head to the overlapping open end regions of the first and second capsule portions thereby to plasticise the overlapping open end regions.

6. The method according to 5, wherein the heat sealing head includes a mould for moulding the plasticised overlapping end regions during the moulding step.

7. The method according to claim 1, wherein the first and second capsule portions are of a fusion weldable material comprising a comestible gelatin based material.

8. A comestible capsule including:
   a first comestible capsule portion having a closed end and an open end;
   a second comestible capsule portion having a closed end and an open end, the second capsule portion being located within the first capsule portion such that a region of the second capsule portion is in overlapping contact with a region of the first capsule portion so as to define a chamber within which a substance is held in hermetic isolation, the capsule being characterized in that overlapping open end regions of the first and second capsule portions are fused to one another so as to form a circumferential fused sealing zone and wherein the fused sealing zone tapers inwardly from an outer side thereof towards a free end of the fused sealing zone.

9. The capsule according to claim 8, wherein the first and second capsule portions are of flexible gelatin.

10. The capsule as claimed in claim 8, wherein the overlapping end regions of the first and second capsule portions are fused to one another by being plasticised such that the fused sealing zone comprises a homogenous sealing zone.

11. The capsule according to claim 10, including an end cap which is located over the open ends of the first and second capsule portions thereby to define an additional chamber within which an additional substance can be held.

12. The capsule as claimed in claim 8, wherein the capsule is manufactured in accordance with the method of claim 1.

13. A sealing apparatus for sealing overlapping open end regions of two comestible capsule portions so as to form a sealed chamber wherein a substance is held in hermetic isolation, each of the capsule portions having an open end and a closed end wherein the closed end of one of the capsule portions is located within the other capsule portion such that the overlapping open end regions are in contact, the sealing apparatus comprising a heat sealing head including a mould defining a mould cavity within which the overlapping open end regions of the capsule portions are received, the heat sealing head being operable to apply heat to the overlapping open end regions in a fusion welding process sufficient to cause plasticising of the overlapping open end regions, causing the end regions to undergo partial phase change thereby to fuse the overlapping open end regions to form a circumferential annular sealing zone, the mould cavity of the heat sealing head, is in the form of a circumferential groove and wherein the mould defines an inner moulding wall, an outer moulding wall and an end moulding wall extending between the inner and outer moulding walls, the inner moulding wall contacting an inner side of the overlapping open end regions of the capsule portions, the outer moulding wall contacting an outer side of the overlapping open end regions of the capsule portions for applying heat to and forming the inner and outer sides of the overlapping open end regions of the capsule portions to form said fused sealing zone, the outer moulding wall defining a moulding face which extends obliquely relative to the outer side of the overlapping open end regions, thereby to bend the overlapping end regions inwardly providing the fused sealing zone with a tapering configuration wherein the fused sealing zone tapers inwardly from an outer side thereof towards a free end of the fused sealing zone.

14. The sealing apparatus according to claim 13, wherein the two capsule portions are of gelatin.

15. The sealing apparatus as claimed in claim 13, wherein the sealing apparatus is configured to seal overlapping end regions of the first and second capsule portion of the capsule in accordance with claim 8.

* * * * *